United States Patent [19]

Moffatt et al.

[11] Patent Number: 5,336,777
[45] Date of Patent: Aug. 9, 1994

[54] PROCESS FOR THE PREPARATION OF ISOTHIAZOLINONES

[75] Inventors: Frank S. Moffatt, Berkshire; David Winstanley, Lancashire, both of England

[73] Assignee: Zeneca Limited, London, England

[21] Appl. No.: 971,809

[22] Filed: Nov. 5, 1992

Related U.S. Application Data

[63] Continuation of Ser. No. 582,261, Sep. 13, 1990, abandoned.

[30] Foreign Application Priority Data

Sep. 20, 1989 [GB] United Kingdom ............... 8921220

[51] Int. Cl.$^5$ ........................................... C07D 275/04
[52] U.S. Cl. ........................................ 548/209; 548/213
[58] Field of Search ............................... 548/209, 213

[56] References Cited

U.S. PATENT DOCUMENTS

| | | | |
|---|---|---|---|
| 4,568,781 | 2/1986 | Effenberger et al. | 568/937 |
| 4,751,311 | 6/1988 | Backhouse | 548/209 |
| 4,851,541 | 7/1989 | Maignan et al. | 548/209 |
| 5,049,677 | 9/1991 | Prout et al. | 548/213 |

FOREIGN PATENT DOCUMENTS 2176187 12/1986 United Kingdom .

Primary Examiner—Joseph P. Brust
Assistant Examiner—Mary Susan H. Gabilan
Attorney, Agent, or Firm—Cushman, Darby & Cushman

[57] ABSTRACT

Compounds of the general formula

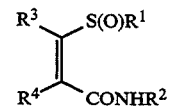

are cyclised to the corresponding isothiazolinone using a carbonyl halide of the formula RCOX where R is halogen or alkyl and X is halogen. $R^3$ and $R^4$ are preferably such as to form a 5 or 6 membered ring. Useful carbonyl halides are phosgene and propionyl chloride. Using acyl halides such as propionyl chloride, a mixture of the isothiazolinone and a salt of the carboxylic acid can be obtained, for example an essentially equimolar mixture of 2-methyl-4,5-trimethyl-4-isothiazolin-3-one and sodium propionate

14 Claims, No Drawings

PROCESS FOR THE PREPARATION OF ISOTHIAZOLINONES

This is a continuation of co-pending application Ser. No. 07/582,261 filed on Sep. 13, 1990, now abandoned.

The present invention relates to a process for the preparation of isothiazolinones, particularly tri- or tetra-methylene-4-isothiazolin-3-ones.

Isothiazolinones are a class of compounds which are known to have useful antimicrobial activity and several compounds of this type are commercially available and are used as industrial biocides, particularly as bactericides.

A new class of isothiazolinones, specifically those of the type 4,5-polymethylene-4-isothiazolin-3-one, are disclosed in GB 2087388. In compounds of this type, the polymethylene chain contains 3 or 4 carbon atoms or is a chain substituted by a lower alkyl radical having from 1 to 4 carbon atoms. These compounds can be prepared by a process wherein a carbamoylcyclanone is converted to the corresponding carbamoylthiocyclanone which is then cyclised to form the desired isothiazolin-3-one product. The first stage of this procedure uses hydrogen sulphide and gaseous hydrogen chloride and the second stage is carried out in an alcohol solution in the presence of sodium metaperiodate previously fixed to acidic alumina.

According to GB 2176187, the procedure GB 2087388 has the disadvantage of being difficult to transfer to the industrial level. As an alternative to the procedure of GB 2087388, GB 2176187 discloses an intermediate product which is a 2-alkylthio- or 2-aralkylthio-1-cycloalkene-1-carboxamide, which can be converted to the corresponding sulphoxide by the action of m-chloroperbenzoic acid, or the action of hydrogen peroxide in an acidic medium, and the resulting sulphoxide can be cyclised to the desired final product, which is 4,5-tri or tetra-methylene-4-isothiazolin-3-one. The sulphoxide is cyclised in a suitable solvent such as methylene chloride in the presence of an acid chloride. The acid chloride specifically disclosed is thionyl chloride, which is used in all of the working examples.

The isothiazolinone is typically precipitated during the cyclisation step and can be separated from the reaction medium and washed to remove any excess thionyl chloride and reaction products such as sulphur dioxide. However, since many isothiazolinones are skin irritants or sensitisers, on a commercial scale separation of solid isothiazolinone has to be effected in a closed vessel and this adds to the production costs. Accordingly we prefer to contact the precipitated isothiazolinone, together with the reaction medium, with water in which the isothiazolinone is soluble giving an aqueous solution of the isothiazolinone which is readily separated from the reaction medium and which gives fewer containment problems. However, using such a procedure, the excess unreacted thionyl chloride can cause the formation of undesirable tars as by-products. Furthermore, thionyl chloride is difficult to separate from the isothiazolinone since the separation is typically effected by distillation and must be effected at a relatively low temperature, preferably not greater than 50° C., in order to avoid decomposition of the isothiazolinone product. Additionally, sulphur dioxide is a by-product of the cyclisation stage using thionyl chloride and is extracted into the aqueous solution where it can cause breakdown of the isothiazolinone. Hence, whilst extraction into water from the reaction medium avoids the need for containment of solid isothiazolinone, it is not satisfactory for commercial use due to problems arising from the presence of unreacted thionyl chloride and of sulphur dioxide by-product.

We have found that the cyclisation step can be effected using other reagents but many of those also give problems due to the formation of undesirable tars, low yield of product or in other ways. However, we have found that certain compounds can be used to effect the cyclisation to give Mood yields of the isothiazolinone product with little if any tar by-products and with no reaction products which cause undesirable breakdown of the reaction product.

According to the present invention there is provided a process for the preparation of an isothiazolin-3-one derivative which comprises cyclising a compound of the general formula I

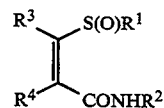

in the presence of an organic solvent and a carbonyl halide of the general formula RCOX, wherein R is a halogen atom or an alkyl group:
$R^1$ is an alkyl group or an aralkyl group;
$R^2$ is a hydrogen atom or an optionally substituted hydrocarbyl group;
$R^3$ and $R^4$ may be the same or different, and are hydrogen, halogen, or an optionally substituted hydrocarbyl group or $R^3$ and $R^4$ together with the carbon atoms to which they are attached, form an optionally substituted ring: and
X is a halogen atom.

The compound of formula I is a sulphinyl carboxamide and may be a compound as described in GB 2176187. The compound of formula I is typically one in which $R^1$ is a group which contains 1 to 12 carbon atoms and very conveniently is one in which $R^1$ is an aralkyl group for example an aralkyl group containing up to 10 carbon atoms and especially a benzyl group. The group $R^2$ may be a hydrogen atom when the product obtained will be an isothiazolinone substituted only by the groups $R^3$ and $R^4$. Alternatively, $R^2$ can be a hydrocarbyl group such as an alkyl, aryl, cycloalkyl, alkaryl, aralkyl or alkenyl group containing up to 20 carbon atoms, especially 1 to 12 carbon atoms. Any substituents present in the group $R^2$ should be such as not to deleteriously affect the properties of the final isothiazolinone product. The substituents may be nitro groups, halogen atoms, oxyhydrocarbon groups or halohydrocarbon groups. Typically the group $R^2$ is unsubstituted and preferably is an alkyl group. Very preferably $R^2$ is a lower alkyl group, that is an alkyl group containing not more than six carbon atoms, for example a methyl group.

Preferably at least one of the groups $R^3$ and $R^4$ is other than hydrogen. If $R^3$ and/or $R^4$ is halogen, it is typically chlorine. If $R^3$ and/or $R^4$ is a hydrocarbyl group, it is typically an alkyl group which contains 1 to 12 carbon atoms. Alternatively, $R^3$ and $R^4$ may form a ring, for example a benzene ring. However, we have found that the process of the present invention is especially useful when $R^3$ and $R^4$ together form a polymethylene group of the type —$(CH_2)_n$— where n is an integer which has a value of at least three. If $R^3$ and/or $R^4$ are substituted or together form a substituted ring, the substituents should be such as not to deleteriously affect the properties of the final isothiazolinone product. Suitable substituents may be nitro groups, halogen atoms, oxyhydrocarbon groups and halohydrocarbon groups. Typically $R^3$ and/or $R^4$ are unsubstituted alkyl groups or together form an unsubstituted ring, especially a cycloalkene ring.

According to a preferred aspect of the present invention, a compound of the general formula II is cyclised

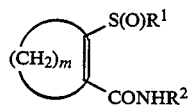   II where $R^1$ and $R^2$ are as previously defined: and m has a value of 3 or 4.

The value of m is typically three since such compounds produce isothiazolinone derivatives which have particularly useful properties as industrial biocides.

The carbonyl halide is conveniently one in which X is chlorine. The group R can be an alkyl group, for example one containing up to 12 carbon atoms, and is preferably a lower alkyl group, as previously defined herein. Alternatively R can be a halogen atom and the preferred halogen atom is chlorine. We have obtained useful results using, as the carbonyl halide, phosgene (R and X are both chlorine) and propionyl chloride (R is an ethyl group and X is chlorine).

Any suitable organic solvent my be used and it is preferred to use solvents which are immiscible with water such as hydrocarbons, halohydrocarbons and higher ethers and ketones. It is generally preferred to use a hydrocarbon solvent, for example a hydrocarbon solvent having a boiling point of at least 50° C. and typically one having a boiling point not exceeding 150° C. The solvent may be a commercially available hydrocarbon mixture and may be an aliphatic or aromatic hydrocarbon, or a mixture thereof. It is generally preferred however that the solvent is an aliphatic hydrocarbon such as a petroleum ether having a boiling point in the range 100° to 120° C.

As indicated previously herein, the isothiazolinone reaction product is susceptible to degradation at elevated temperatures. Furthermore, we have found that the yield of the isothiazolinone product is reduced at higher reaction temperatures. Hence, it is preferred that the cyclisation process of the present invention is effected at a temperature of not more than 50° C. and preferably not more than 30° C. If the carbonyl halide is an acyl halide such as propionyl chloride, it is generally preferred that the reaction temperature does not exceed 20° C. and especially is not more than 10° C., We have found that there is an exotherm during the cyclisation step and this can result in a temperature rise of about 10° C. Accordingly, the reaction mixture is very desirably agitated throughout the reaction and is cooled in order to prevent an excessive temperature rise. We have obtained satisfactory yields of product when using an acyl halide and affecting the reaction at an initial temperature of 0°–5° C. In order to control the temperature, and to minimise the effects of the reaction exotherm, it is convenient to add the carbonyl halide to the sulphinyl carboxamide of formula I, or especially formula II, over an extended period of time, for example 15 minutes to three hours, conveniently one hour using an acyl halide.

If the carbonyl halide is phosgene, this may be used in the gaseous state by bubbling through the liquid reaction medium or may be cooled and condensed and added dropwise to the reaction medium over an extended period of time which is conveniently two hours.

The cyclisation reaction occurs readily and typically is complete between 0.5 and 3 hours, for example one to two hours, after the addition of the carbonyl halide has finished. The progress of the reaction can be monitored by suitable analytical means, for example by high performance liquid chromatography.

The sulphinyl carboxamide and carbonyl halide are preferably reacted together in essentially equimolar amounts or using a slight molar excess of the carbonyl halide. Thus, the molar proportions of sulphinyl carboxamide to carbonyl halide are typically in the range 2:1 to 1:2, and especially are in the range 1:1 to 1:1.5, particularly 1:1.05 to 1:1.2.

When the cyclisation reaction is complete, the product mixture is conveniently mixed with water, preferably at least an equal volume of water. The isothiazolinone product is extracted into the water to form an aqueous solution and the amount of water used should be sufficient to dissolve all of the isothiazolinone product. Reaction by-products extracted into the aqueous phase may be removed by washing the aqueous solution with a suitable organic solvent which is conveniently the same material as is used as the solvent for the cyclisation reaction.

The aqueous phase typically contains a weakly associated salt of the isothiazolinone together with an acid derived from the carbonyl halide, for example hydrochloric acid or propionic acid. The aqueous phase is preferably neutralised in order to avoid degradation of the product on storage, particularly in the presence of strong mineral acid.

The neutralisation may be effected using any suitable base. Since the isothiazolinone product is sensitive to strongly alkaline conditions, it is preferred to agitate the mixture vigorously during the addition of the base. The base is conveniently an aqueous solution of an alkaline metal hydroxide, for example sodium hydroxide. Neutralisation is effected to give a pH which is in the range 4 to 9 and especially is not more than 7.5, for example in the range 6.5 to 7.5. During the neutralisation it is preferred that the temperature should not be allowed to rise excessively and it is especially preferred that the temperature does not exceed 25° C.

The aqueous solution contains the isothiazolinone and a salt of an acid derived from the carbonyl halide. The relative molar proportions of the isothiazolinone and the salt are similar to the proportions of sulphinyl carboxamide and carbonyl halide used to effect the cyclisation reaction. Hence, the aqueous solution typically contains the isothiazolinone and the salt in essentially equimolar proportions, and in general with a slight molar excess of the salt.

The salt may be a salt of a carboxylic acid, for example sodium propionate.

A particular useful aqueous solution contains a 4,5-polymethylene-4-isothiazolin-3-one together with a salt of the general formula $MOCOR^5$ where M is an alkali metal; and
$R^5$ is an alkyl group.

M is conveniently sodium. The group $R^5$ is derived from the carbonyl halide and corresponds to the group R when this is an alkyl group. A particular salt is sodium propionate (M is sodium and $R^5$ is ethyl).

The process of the present invention may be used to obtain 4,5-polymethylene-4-isothiazolin-3-ones as described in GB 2087388. Using the process of the present invention we have obtained 2-methyl-4,5-trimethylene-4-isothiazolin-3-one in good yields. In particular, we have obtained an aqueous solution containing 2-methyl-4,5-trimethylene-4-isothiazolin-3-one and sodium propionate. Such a solution typically contains essentially equimolar proportions of the isothiazolinone and the salt, and especially contains a slight molar excess, of up to 1.5 moles, of the salt.

The aqueous solution may be diluted to give a desired concentration of the isothiazoiinone, for example from 1 to 10% by weight of isothiazoinone. The solution may be used as an industrial biocide, particularly as a bactericide, as is disclosed on GB 2087388.

The present invention is described in more detail hereafter in the following illustrative, non-limiting examples.

EXAMPLE 1

Into a 150 cm³, 4-necked glass reaction flask fitted with an anchor agitator, thermometer, dropping funnel and condenser were charged 75 g of petroleum ether (100–120). 34.72 g of N-methyl-2-benzylsulphinyl-1-cyclopentene-1-carboxamide of 94.7% purity (obtainable as described in GB 2176187) were then charged to the petroleum ether in the reaction flask with agitation and the suspension was cooled to 0°–5° C.

12.72 g of propionyl chloride were charged to the suspension over a period of one hour, maintaining the temperature at 0°–5° C. throughout. The suspension was agitated for a further one hour when high performance liquid chromatography analysis showed the reaction to be complete.

230 cm³ of water were charged to a 500 cm³ flask having an agitator and a bottom run-off and the flask and its contents were cooled to 10°–15° C. with agitation. The suspension obtained as described previously was then added to the water whilst continuing to agitate the contents of the flask. Agitation was stopped, the two layers were allowed to separate and the lower aqueous layer containing the isothiazolinone product was run off. This layer was washed twice with petroleum ether (100–120), using 4.5 g for each wash, to remove traces of benzyl chloride. The petroleum ether solutions were combined for solvent recovery and disposal of benzyl chloride.

The separated aqueous layer was adjusted to pH 7 with 47% by weight caustic soda liquor with efficient agitation, maintaining the temperature at below 25° C. throughout. One gramme of a diatomaceous earth filter aid and one g of activated carbon were then charged, the mixture was filtered and a small follow through water wash applied.

By analysis, the final aqueous solution was found to contain 2-methyl-4,5-trimethylene-4-isothiazolin-3-one and sodium propionate, the latter component being in a slight molar excess. 17.46 g of the 2-methyl-4,5-trimethylene-4-isothiazolin-3-one were obtained, representing a yield of 90% of theory based on the N-methyl-2-benzylsulphinyl-1-cyclopentene-1-carboxamide starting material.

EXAMPLE 2

Into a 500 cm³, 4-necked, glass reaction flask fitted with an anchor agitator, thermometer, dropping funnel and condenser were charged 150 g of petroleum ether (100–120). The contents of the flask were agitated and 86.51 g of N-methyl-2-benzylsulphinyl-1-cyclopentene-1-carboxamide of 91.2% purity (obtainable as described in GB 2176187) were added and the temperature was adjusted to 25 to 30° C.

36.12 g of phosgene was condensed to the liquid phase using a condenser cooled with a solid carbon dioxide/ethanol mixture. This liquid phosgene was charged to the reaction flask dropwise over a period of two hours whilst continuing to agitate and maintaining the temperature at 25° to 30° C. by external cooling.

Completion of the reaction was tested using high performance liquid chromatography analysis. Reaction was found to be complete after agitation for a further two hours at 25° to 30° C. after all of the phosgene had been added.

Residual phosgene in the product mixture was removed by the passage of a stream of nitrogen through the product mixture over a period of one hour. 120 cm³ of water were then added to the mixture at 25° C.

355 cm³ of water were charged to a one dm³ flask having an agitator and a bottom run off. The flask and its contents were maintained at 20° to 25° C., and the contents were agitated during the addition of the reaction mixture plus water obtained as previously described. Agitation was terminated and the liquid phases were allowed to separate. The lower aqueous layer which contained the isothiazolinone product was run off. This layer was then extracted with 50 g of petroleum ether (100–120) to remove residual by-product benzyl chloride.

The separated aqueous later was adjusted to pH 4 to 6 by the slow addition of 47% by weight caustic soda liquor whilst agitating efficiently and maintaining the temperature at below 25° C.

2 g of activated carbon and 2 g of a diatomaceous earth filter aid were added to the agitated aqueous solution, which was then filtered. The filtered solution was diluted to give a 6% by weight concentration of 2-methyl-4,5-trimethylene-4-isothiazolin-3-one. By analysis it was determined that the yield of the isothiazolinone was 93.7% of theory based on the N-methyl-2-benzylsulphinyl-1-cyclopentene-1-carboxamide starting material.

I claim:

1. A process for the preparation of an aqueous solution of an isothiazolin-3-one derivative which comprises
(a) reacting a compound of the general formula II

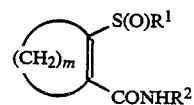

II in the presence of a water immiscible organic solvent with a carbonyl halide of the formula RCOX; wherein:
R is a halogen atom or an alkyl group;
$R^1$ is an alkyl group of an aralkyl group;
$R^2$ is a hydrogen atom or an optionally substituted hydrocarbyl group;
m is 3 or 5; and
X is a halogen atom;

to form a cyclised product mixture comprising an isothiazolin-3-one derivative;

(b) mixing the above product mixture with water to extract the isothiazolin-3-one derivative from the water immiscible organic solvent into water; and (c) separating the two phases to obtain an aqueous solution of the isothiazolin-3-one derivative.

2. The process of claim 1 wherein compound II is one in which the group $R^1$ contains 1 to 12 carbon atoms.

3. The process of claim 1 or claim 2 wherein $R^1$ is an aralkyl group.

4. The process of claim 1 wherein compound II is one in which the group $R^2$ is an alkyl group containing not more than six carbon atoms.

5. The process of claim 1 wherein the compound of the general formula II is one in which the value of m is three.

6. The process of claim 1 wherein the carbonyl halide is one in which X is chlorine and R is chlorine or an alkyl group containing up to 12 carbon atoms.

7. The process of claim 8 wherein the carbonyl halide is phosgene or propionyl chloride.

8. The process of claim 1 which is effected at a temperature which does not exceed 30° C.

9. The process of claim 8 wherein the carbonyl halide is an acyl halide and the initial temperature is in the range 0° to 5° C.

10. The process of claim 1 wherein compound II and the carbonyl halide are used in the molar proportions from 2:1 to 1:2.

11. The process of claim 1 wherein the reaction mixture is neutralised using a base to give a pH of not more than 7.5.

12. The process of claim 1 wherein compound II is N-methyl-2-benzylsulphinyl-1-cyclopentene-1-carboxamide and the carbonyl halide is phosgene or propionyl chloride.

13. The process of claim 1 wherein the aqueous solution obtained in step (c) is washed with an organic solvent to remove the reaction by-products.

14. The process of claim 1 wherein the aqueous solution obtained in step (c) is neutralized with a base.

* * * * *